Figure 1:
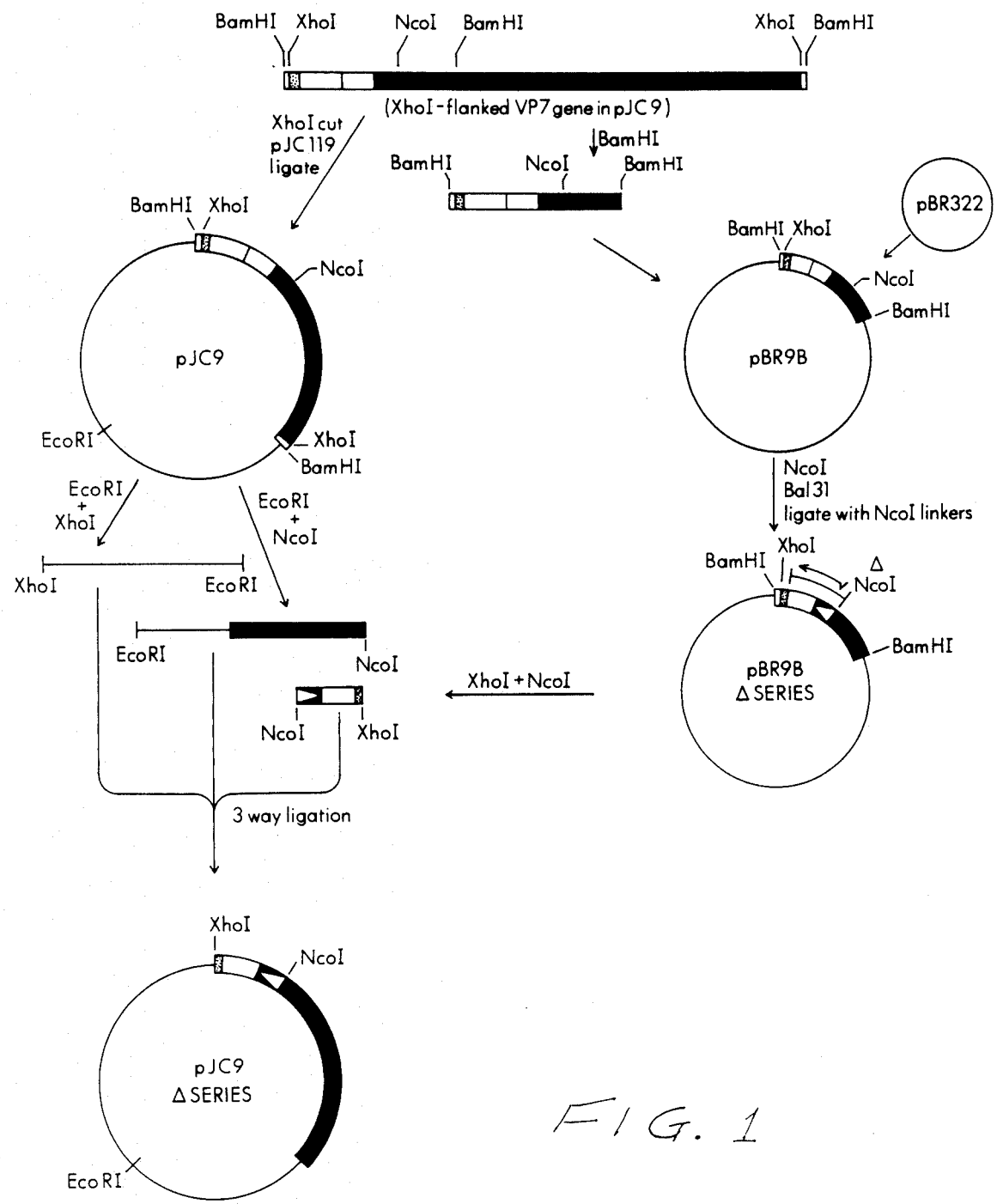

United States Patent [19]

Atkinson et al.

[11] Patent Number: 4,861,864

[45] Date of Patent: Aug. 29, 1989

[54] ROTAVIRUS ANTIGENS

[75] Inventors: Paul H. Atkinson, New York, N.Y.; A. Richard Bellamy, Auckland, New Zealand; Gerald W. Both, Northride, Australia; Chiara Tyndall, Mosman, Australia; Marianne S. Poruchynsky, Bronx, N.Y.

[73] Assignee: Albert Einstein College of Medicine of Yeshiva University (a Div. of Yeshiva University), Bronx, N.Y.

[21] Appl. No.: 206,916

[22] Filed: Jun. 13, 1988

Related U.S. Application Data

[63] Continuation of Ser. No. 768,971, Aug. 23, 1985, abandoned, and a continuation-in-part of Ser. No. 768,395, Aug. 22, 1985, abandoned.

[30] Foreign Application Priority Data

May 14, 1985 [AU] Australia ............................ P400542

[51] Int. Cl.[4] .......................... C07K 7/10; C07K 13/00
[52] U.S. Cl. .................................... 530/324; 530/350; 424/88; 424/89
[58] Field of Search .................. 530/324, 350; 424/88, 424/89

[56] References Cited

PUBLICATIONS

Chem. Abstr., vol. 104, (1986), 223138.
Chem. Abstr., vol. 103, (1985), 34597.
Chem. Abstr., vol. 102, (1985), 92595.
Chem. Abstr., vol. 99, (1983), 209362.
Chem. Abstr., vol. 100, (1984), 117536.
Chem. Abstr., vo. 100, (1984), 117536.
Chem. Abstr., vol. 106, (1987), 194265.
Chem. Abstr., vol. 106, (1987), 169950.
Chem. Abstr., vol. 105, (1986), 222513.
Chem. Abstr., vol. 104, (1986), 46516.
Chem. Abstr., vol. 104, (1986), 146775.
Chem. Abstr., vol. 104, (1986), 86653.
J. of Virology, (1985), 791-797, vol. 54.
Chem. Abstr., vol. 104, (1986), 46459a.

Primary Examiner—Delbert R. Phillips
Attorney, Agent, or Firm—Amster, Rothstein & Ebenstein

[57] ABSTRACT

A soluble form of the neutralizing antigen or rotavirus is provided. The antigen is formed by cloning DNA coding for VP7 protein into an expression vector and preparing deletion mutants coding for a soluble cell secreted neutralizing antigen. The preparation of the deletion mutants includes the removal of the DNA sequences coding for those amino acids of the VP7 protein responsible for its normal intracellular location and non-secretion characteristics. The deletion mutant may be used in the formation of stably transformed animal cell lines which contiuously secrete the antigen, or in the production of certain yeast strains which produce the soluble antigen with appropriate glycosylation.

12 Claims, 5 Drawing Sheets

ROTAVIRUS ANTIGENS

This application is co-pending application Ser. No. 768,971, filed Aug. 23, 1985, now abandoned, and a continuation-in-part of application Ser. No. 768,395, filed Aug. 22, 1985, now abandoned.

This application is a continutation-in-part of application Ser. No. 768,345 filed Aug. 22, 1985.

The work described in this application was supported by grants from the U.S.P.H.S., National Institutes of Health under grant #CA 13402, Core Cancer Grant CA 13330, and grants from the New Zealand Medical Research Council and the Diarrhoeal Diseases Control Programme of the World Health Organization.

The present invention relates to the antigens of rotavirus and more particularly to a soluble, cell secreted version of the neutralizing antigen of rotavirus, such as a modified VP7 protein.

Acute diarrhoeal disease is an important health problem, both in developed countries such as New Zealand, Australia, Japan and the U.S.A. and in the underdeveloped nations. Recent evidence has indicated that the majority of diarrhoeal episodes in infants and young children are virus-induced. Rotaviruses are now known to be by far the most common cause of virus-induced diarrhoea ('winter diarrhoea'). They are the viruses most frequently observed in almost all areas of the world where the stools of children suffering from diarrhoea are examined.

In developing countries, diarrohoeal disease is a major cause of mortality and mobidity. World Health Organization statistics indicate that diarrhoeal disease accounts for a large proportion of the total number of deaths in many countries of the world. For Asia, Latin America and Africa, it has been estimated that 3 to 5 billion cases and 5 to 10 million deaths are caused by diarrhoea each year.

For many developed countries rotaviruses are the most important etiologic agents causing acute gastroenteritis in young children. Where the disease has been studied in any detail, up to 63% of the hospital admissions for childhood diarrhoea have proved to be rotavirus-positive.

The genome of rotaviruses consists of eleven segments of double-stranded RNA and six of these segments code for viral structural polypeptides. These viral proteins are arranged in a double-layered capsomere, the intact virion presenting two major proteins of the exterior (VP3, VP7): the inner core (sometimes termed the single-shelled particle) presents one (VP6). The relative importance of these three viral proteins in eliciting the immune response that follows virus infection is not yet clear, but the situation has been clarified somewhat by the discovery that VP6 constitutes the group and subgroup antigen and VP7 the determinant of serotype specificity.

VP7 is a 38,000 MW glycoprotein which is the translational product of genomic segment 9. This protein is known to constitute the major neutralizing protein (it induces the formation of neutralizing antibodies) because genetic studies have revealed that neutralization segregates with segment 9.

Since VP7 is the viral protein against which neutralizing antibodies are directed, it is a prime candidate for the development of a rotavirus vaccine affording protection through a single viral protein. However, the VP7 protein is unusual in that, unlike many other viral glycoproteins, it is neither secreted by the cell or transported in the cell to be extruded and anchored in the surface membrane. In fact, there is no evidence of intracellular transport of VP7 in an infected cell. Specifically, VP7 is an integral membrane protein with a lumenal orientation. This protein associates with viral cores that bud into the lumen of the rough endoplasmic reticulum ("RER") from cytoplasmic structures, called viroplasms. Mature virus remains within the lumen of the RER until their release by cell lysis.

VP7 is an integral membrane glycoprotein which is located in the endoplasmic reticulum ("ER"). The Golgi apparatus is not involved in processing the mature form of VP7, a fact confirmed by the presence on the molecule of the high-mannose form of carbohydrate. VP7 therefore constitutes an example of an insoluble membrane glycoprotein that is targeted to the ER and is not subsequently directed further along the secretory pathway. The cells infected with rotavirus therefore do not secrete the neutralizing antigen VP7 and, consequently, the immune system is likely to see the protein only when infected cells lyse and the virus is released. As a result, VP7 is not readily disseminated throughout the body and therefor not greatly exposed to the immune system. Further, VP7 is insoluble in aqueous solutions and difficult to purify, thereby impeding the formation of a vaccine.

Accordingly, it is a object of the present invention to provide a soluble form of the neutralizing antigen of rotavirus.

Another object of the present invention is to provide a soluble cell secreted form of the neutralizing antigen of rotavirus.

Still another object of the present invention is to provide a neutralizing antigen to rotavirus which is readily disseminated throughout the body with the concomitant greater exposure to the immune system.

A further object of the present invention is to provide a rotavirus antigen in the form of a modified VP7 protein which is soluble.

A still further object of the present invention is to provide a soluble form of the neutralizing antigen of rotavirus capable of forming the basis of an effective vaccine.

An additional object of the present invention is to provide cell lines which are stably transformed so as to continuously secrete soluble neutralizing antigen of rotavirus.

An additional object of the present invention is to provide yeast strains which are stably transformed so as to continuously secrete soluble neutralizing antigen of rotavirus.

An additional object of the present invention is to provide a DNA sequence coding for the expression of a soluble cell secreted form of the neutralizing antigen of rotavirus.

In accordance with the present invention a soluble form of the neutralizing antigen of rotavirus is provided. The antigen is formed by cloning DNA for VP7 protein into an expression vector and preparing deletion mutants coding for a soluble cell secreted form of the neutralizing antigen. The preparation of the deletion mutants includes the removal of the DNA sequences coding for those amino acids of the VP7 protein responsible for its normal intracellular location and non-secretion characteristics. The resultant secreted soluble mutant VP7 neutralizing antigen may form the basis of a rotavirus vaccine since it is readily disseminated throughout the body and accessible to the immune system.

An additional feature of the invention is the formation of cell lines which are stably transformed with a deletion mutant coding for a soluble cell secreted neutralizing antigen of rotavirus whereby the cell line continuously secretes the antigen, and the production of yeast strains which produce the soluble antigen with appropriate glycosylation.

Figure 2:
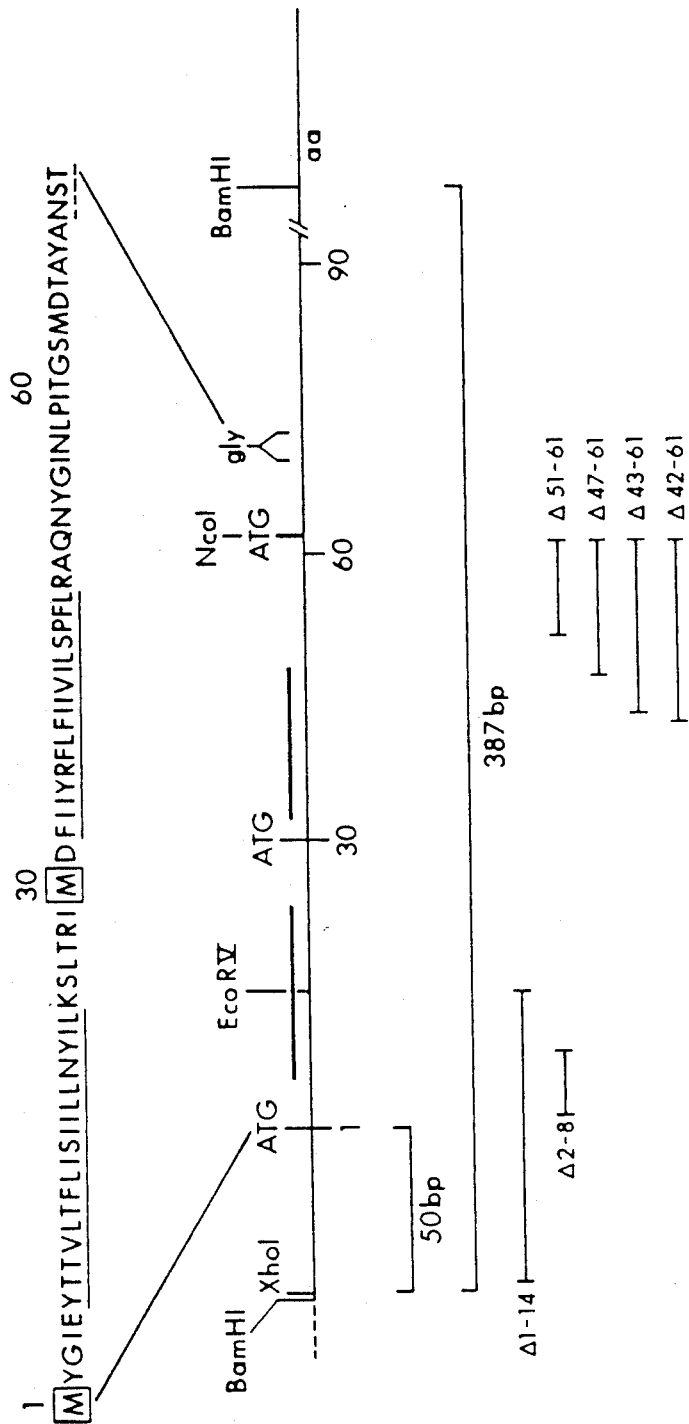
Figure 3:
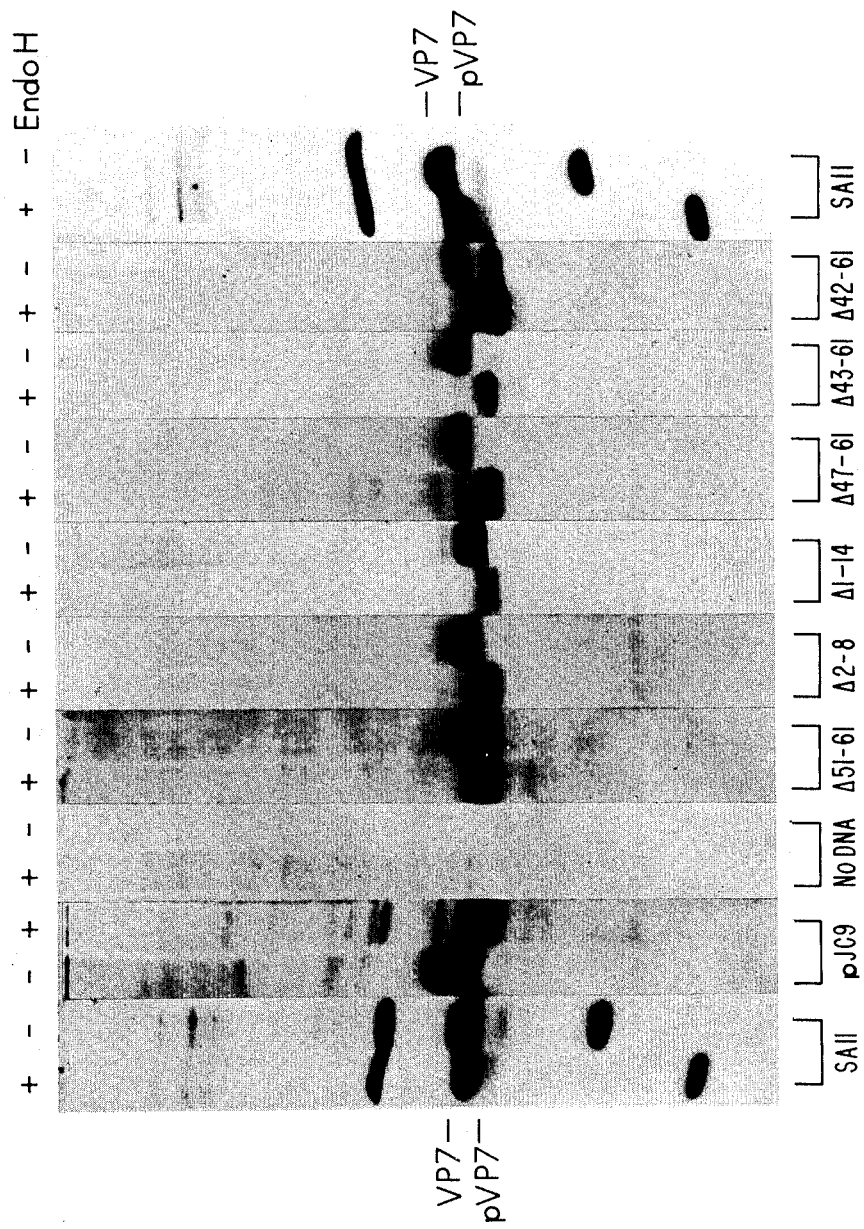
Figure 4:
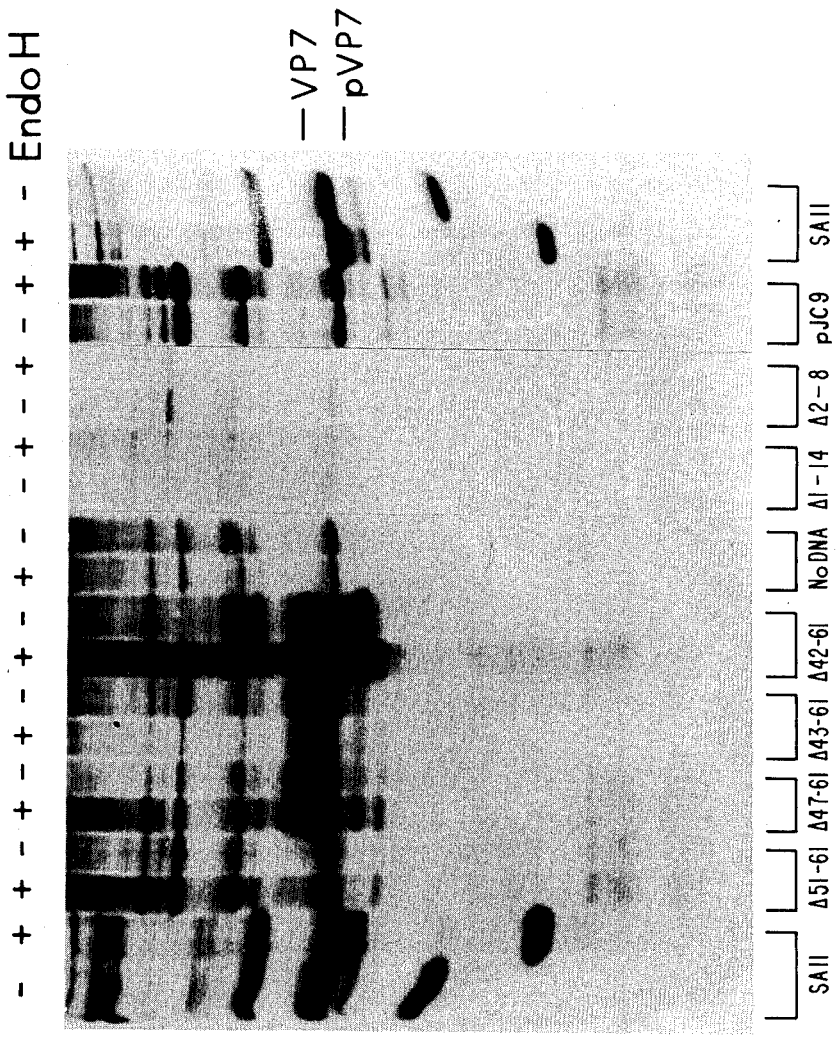
Figure 5:
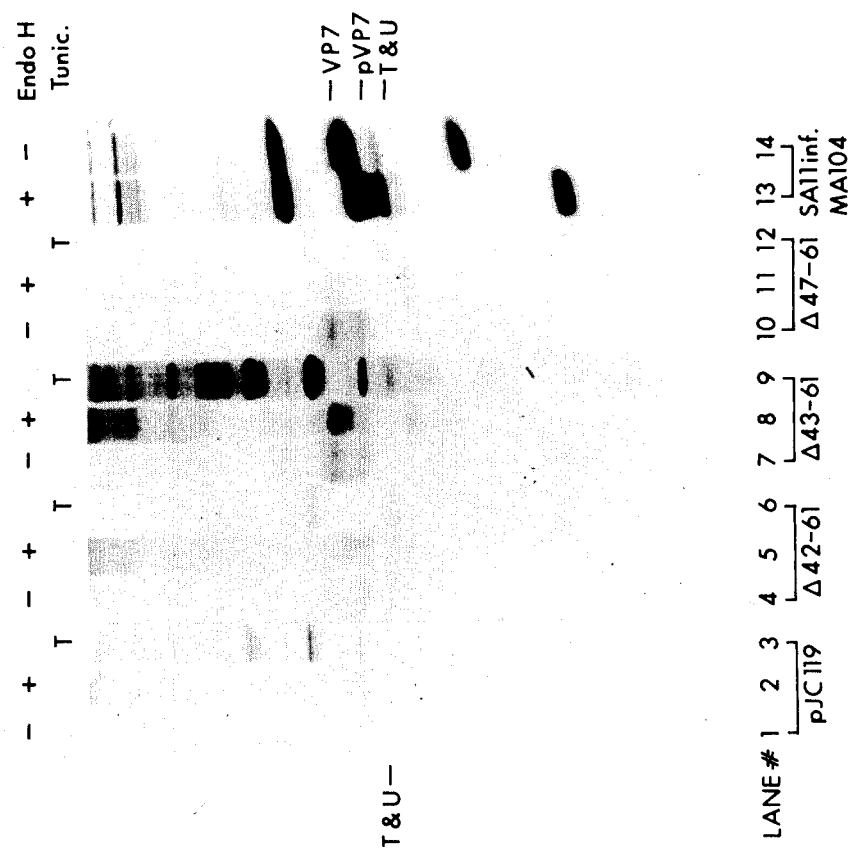

These and other objects and features of the invention will be further understood by reference to the following detailed description of the presently preferred embodiment of the invention taken in junction with the drawings, in which:

FIG. 1 is a diagram showing the strategy for the construction of VP7 gene deletions in an SV40 expression vector. Solid bars are VP7 coding sequences. Open bars represent the location of VP7 hydrophobic domains. Thin lines are pBR322 and SV40 sequences. The stippled area corresponds to the 50 bp noncoding region of the VP7 gene 5' to the ATG;

FIG. 2 shows the structure of the 5' end of the VP7 gene showing the location of deletion mutants within it and the amino terminal sequence of the protein. The hydrophobic domains underlined in the amino acid sequence are those generally accepted in the art, but may vary if other criteria are applied. The single glycosylation site is located at residue 69. The deletions are numbered according to the amino acid residues actually deleted. Due to the addition of Nco 1 linkers in the constructions, Ser at position 61 is changed to Ala in all mutants numbered N-61. In the complete VP7 clone used for these studies, two conservative amino acid changes occurred. Namely, $C_{32}$ and $L_{37}$ are both changed to F;

FIG. 3 shows the Endo-H sensitivity of intracellular products of cells transfected with full length and mutated VP7 genes. Cells were labeled for 4 hrs with L-$^{35}$S-methionine, the VP7 proteins immunoprecipitated ((−) tracks), and half of the samples digested with Endo-H ((+) tracks). Total SA11-infected MA104 cell lysate before (−) and after (+) Endo-H is shown as a marker to indicate the position of the glycosylated (VP7) and digested (pVP7) versions of VP7;

FIG. 4 shows the Endo-H sensitivity of immunoprecipitated products from the media of cells transfected with wild type and mutated VP7 genes. Cells were labeled for 4 hrs with L-$^{35}$S-methionine, the medium from each culture subjected to immunoprecipitation ((−) tracks) and half of the samples digested with Endo-H((+) tracks). Total SA11 infected MA104 cell lysate+and −Endo-H displays marker glycosylated (VP7) and digested (pVP7) proteins; and FIG. 5 shows the secretion of mutant VP7 proteins in the presence of tunicamycin. Cells transfected with pJC119 (Lanes 1–3); mutant 42–61 (Lanes 4–6); 43–61 (Lanes 7–9); or 47–61 (Lanes 10–12) were labeled with L-$^{35}$S-methionine for 4 hrs. Where indicated (T), tunicamycin (2ug/ml) was added for the last 8 hrs of transfection. VP7 proteins were immunoprecipitated from the medium ((−) tracks) and digested with Endo-H as indicated ((+) tracks). Total SA11 infected MA104 cell lysate+and - Endo-H is shown. (U) Unglycosylated VP7 proteins.

Rotavirus, a non-enveloped reovirus, buds into the rough endoplasmic reticulum (RER) and transiently acquires a membrane. The structural glycoprotein, VP7, a 38kd integral membrane protein of the endoplasmic reticulum (ER), presumably transfer to virus in this process. The gene for VP7 potentially encodes a protein of 326 amino acids which has two tandem hydrophobic domains at the amino-terminus, each preceded by an in-frame ATG codon. Glycosylation of VP7 is sensitive to endo-B-N-acetylglucosaminidase H (Endo-H).

A series of deletion mutants constructed from a full length cDNA clone of the Simian 11 rotavirus VP7 gene were expressed in COS 7 cells. Products from wild type and mutants which did not affect the second hydrophobic domain of VP7, were localized by immunofluorescence to elements of the ER only. However, mutants affecting the second hydrophobic domain showed immunofluorescent localization of VP7 which coincided with that of wheat germ agglutinin (WGA), indicating transport to the Golgi apparatus. Immunoprecipitable wild-type protein, or an altered protein lacking the first hydrophobic sequence, remained intracellular and Endo-H sensitive. In contrast, products of the mutants affecting the second hydrophobic domain were soluble, transported from ER and secreted. Glycosylation of the secreted molecules was inhibited by tunicamycin, resistant to Endo-H digestion and therefore of the N-linked complex type. Specifically, the VP7 proteins secreted by these mutants acquired complex carbohydrate, as distinct from the high-mannose type exhibited by wild type VP7, showing that they traversed the secretory pathway to the Golgi apparatus. An unglycosylated version of VP7 was also secreted. The second hydrophobic domain appears to contribute to a positive signal for ER location and a membrane anchor function. Secretion of the mutants implies that transport of glycoproteins can be constitutive with their destination being dictated by an overriding compartmentalization signal.

I. cDNA Cloning and Construction of a Plasmid for VP7 Expression

Standard molecular cloning techniques were employed in the cDNA cloning and construction of a plasmid for VP7 expression. The methods described by Maniatis et al in the publication "Molecule Cloning, A Laboratory Manual," Cold Spring Harbour Press (1982), are preferred. The complete sequence of genomic segment nine of Simian 11 rotavirus, was obtained using a partial length cDNA clone that lacked 5'-terminal sequences. A full length clone was isolated using a known cloning strategy such as that described by Gunn et al in the publication "Rotavirus Neutralizing Protein VP7: Antigenic Determinants Investigated by Sequence Analysis and Peptide Synthesis," *J. Virol.*, 54:791–797 (1985). This yielded a VP7 clone inserted in the Pst I site of pBR322 which was confirmed as full length by terminal sequence analysis. The insert was excised with Pst I, digested with nuclease Bal 31 to remove G:C homopolymer tails and the blunt-ended molecule was flanked with Xho I sites by the addition of phosphorylated XhoI linkers. The VP7 gene with Xho I termini was then inserted into the unique Xho I site of pJC119 to yield plasmid pJC16 which contained the rotavirus VP7 sequence in the correct orientation downstream from the SV40 late promoter. Sequencing revealed that pJC16 nevertheless contained residual homopolymeric sequences (15G residues) at the 5' end of the gene. These were removed by replacing the 5'-terminal region of the clone proximal to the Nco I site with a fragment that lacked the residual homopolymeric tail. An Aha III-Nco I fragment was prepared from the SA11 VP7 clone, Xho I linkers were added to the Aha III end, and after recutting, the Xho I-NcoI fragment was cloned into the SV40 vector to generate the plasmid pJC9 (FIG. 1).

II. Preparation of deletion mutants of VP7

Referring now to FIG. 1, pJC9 was cut with Bam Hl and the 387 bp 5'-terminal fragment of the VP7 gene was subcloned into the Bam Hl site of pBR322 to generate pBR9B which contains a unique NcoI site. The plasmid was made linear by cutting with NcoI and digested with Bal 31 to remove nucleotides progressively. The products were made blunt ended, Nco I linkers were added and the plasmids were religated to generate a series of deleted variants of pBR9B. These were sequenced from the NcoI site in order to identify those carrying appropriate in-frame deletions. The small XhoI/Nco I fragments containing modified 5' regions of the gene were retrieved and incorporated into the expression vector (pJC9) by a three-way ligation shown in FIG. 1. Another mutant (1–14), which deleted the first ATG and therefore the first hydrophobic domain, was prepared as follows. Xho I linkers were added to an Eco RV/Bam Hl fragment (FIGS. 1 and 2). This fragment was cut with Xho I and Nco I and the smaller Xho I/Nco I fragment isolated. This segment was then reincorporated into pJC9 by the three way ligation method described above. Mutant 2-8 was construed as follows: The oligonucleotides 5'CATGGTT-CTAACCTTTCTGATAT 3' and 5'CGATAT-CAGAAAGGTTAGAAC 3' were made using a DNA synthesizer. These are complementary and create Nco I and Cla I compatible termini when annealed. The oligonucleotides were phosphorylated and ligated with the EcoRl-Xho I fragment from pJC9 (FIG. 1) and a fragment from the same plasmid, which extended through the VP7 gene, counterclockwise from the EcoR I site to the Cla I site near the 5' end of the gene. The fourth fragment which permitted the vector to circularize was an Xho I - Nco I fragment to 53 bases derived from a pBR9B deletion mutant (FIG. 1), where the Bal 31 digestion went precisely to the first ATG codon. This construction deleted the first eight amino acids of VP7 which are conserved between human, simian, and bovine rotaviruses, and substituted Met-Ala-Met such that the final N-terminal sequence now reads as Met-Ala-Met-Val-Leu Thr . . .

III. Polyclonal Antigen-VP7 Antiserum

SA11 rotavirus was propagated and purified by standard procedures known in the art, such as those described by Street et al in the article "Sequence Diversity of Human Rotavirus Strains Investigated by Northern Blot Hybridization Analysis," *J. Virol.*, 43: 369–378 (1982). Intact double-shelled virions labeled with $^{125}I$ were concentrated by ultracentrifugation and disrupted by boiling in a sodium dodecyl sulfate (SDS) dissociation buffer containing 2-mercaptoethanol. Viral polypeptides were resolved by electrophoresis on discontinuous slab gels and the band corresponding to VP7 located by radioautography. The region of the gel containing the SDS-denatured VP7 was recovered, homogenized with incomplete Freund's adjuvant and injected subcutaneously into rabbits. Animals were boosted at 4 week intervals and the antiserum confirmed as monospecific by Western blot analysis.

IV. Cell Growth, Transfection, Tunicamycin Treatment and Radiolabeling

The RR1 strain of *E. coli* was used for the propagation of all plasmid DNA used for transfections. After standard bacterial lysis procedures, DNA was isolated and purified by cesium chloride-ethidium bromide ultracentrifugation followed by precipitation and resuspension in water. The procedure for transfection of COS 7 cells is generally known in the art. COS 7 cells were grown on 100mm dishes in Dulbecco's modified Eagle's medium (DMEM), containing 5% each of calf and fetal calf serum, 100 U/ml penicillin, 100 mcg/ml streptomycin and 2mMl-glutamine. Monolayers that were 60–80% confluent were washed and transfected in Tris-buffered saline. DNA (15–30 ug/ml) was added to each plate followed by the addition of DEAE-dextran $MW = 2 \times 10^6$, 500 ug/ml). After 1.5–2 hrs at 37° C., the Tris-buffered saline solution was removed and DMEM, containing serum as above and 100 uM chloroquine, was added to the cells. Following incubation for 3 hrs. at 37° C., DMEM without chloroquine but containing serum and additions as above was added. At 45 hrs after DNA/DEAE-dextran removal, the cells were incubated at 37° C. for 1 hr in DMEM salts lacking serum and methionine but supplemented with all other amino acids and 1mg/ml glucose. Transfected cells were then labeled for 2.5 or 4 hrs at 37° C. on a rocker platform in the above medium to which L-$^{35}S$-methionine at a concentration of 150 uCi/ml was added. At the end of the labeling period the medium was collected and nonadherent cells were pelleted by centrifugation in a centrifuge for 10 min. Supernatants were removed and analyzed for expressed secreted material.

For those cells treated with tunicamycin, dishes were incubated in medium containing tunicamycin, at a final concentration of 2ug/ml, beginning at 42.5 hours after transfection and continuing for 8 hours thereafter. Tunicamycin was therefore present for 4 hours prior to radiolabeling, including the one hour preincubation in medium lacking methionine, as well as during the four hour labeling period.

V. Immunoprecipitation

Cell monolayers were rinsed in ice cold phosphate buffered saline (PBS), harvested and lysed in buffer containing 1% each of deoxycholate and Triton X-100, 0.1% SDS and 0.15 M NaCl in 25 mM Tris-HCl pH 8.0 containing 100 units/ml Traysylol. The nuclei were pelleted following the addition of more detergent. Standard procedures were employed for immunoprecipitation of proteins from the post nuclear supernatant by rabbit polyclonal antiserum to VP7 and Protein-A conjugated Sepharose CL4B (PAS). Beads were swollen in distilled water and added to transfected cell lysates before incubation with antibody. PAS beads were pelleted by centrifugation and discarded in an attempt to eliminate any nonspecifically adherent proteins. Polyclonal anti-VP7 serum was then added to lysates which were incubated at 4° C. overnight before the addition of PAS beads. These had been pre-incubated for several hours in a solution containing 10mg/ml bovine serum albumin and a post-nuclear cell lysate of unlabeled, untransfected COS 7 cells.

Medium from the transfected cell cultures was supplemented with an equal volume of 2x lysis buffer containing 1 mM methionine and 1 mg/ml bovine serum albumin. Rabbit polyclonal anti-VP7 serum was added to each in incubated overnight at 4° C., followed by the addition of preabsorbed PAS beads. In an effort to reduce background bands from the media in other experiments, such as that examining the effect of tunicamycin, PAS beads were additionally preabsorbed with media from COS 7 cell cultures. Beads were pelleted from all samples and washed extensively in buffers containing detergent and then in PBS. After boiling the beads in 0.05 M Tris-HCl, pH 6.7 containing 1% SDS to remove the bound antibody protein complexes, 0.2M citrate-phosphate buffer pH5.0 was added prior to treatment of half of each sample with 0.041 units of Endo-H at 37° C., for 1 hour. Preparation of the endoglycosidase H was by the method described by Tarentino and Maley in the article "Purification and Properties of an Endo-B-N-Acetylglucosaminidase Acetylglucosaminidase From *Streptomyces griseus*," *J. Biol. Chem.*, 249:811-817 (1974). A lysate of $L^{35}S$-methionine-labeled SA11-infected MA104 cells was prepared and treated with Endo-H for use as a marker. The reactions were stopped by addition of buffer containing 100 mM Tris, 5% SDS, 1 mM EDTA, 50 mM DTT, 10% glycerol, 0.1% bromophenol blue, 100 ug/ml soybean trypsin inhibitor, 200 U/ml Traysylol, 5 mM B-aminocaproic acid, 1 mM benzamidine, and 2 mM phenylmethylsulfonyl fluoride. Samples were boiled for 3 mins. and analyzed by SDS-polyacrylamide gel electrophoresis on 12% gels run at constant voltage. Gels were fixed, fluorographed in Amplify for 20 mins., dried and then autoradiographed at −70° C. using Kodak SB 5 film.

VI. Immunofluorescent Localization and Electron Microscopy

COS 7 cells which had been grown to semi-confluency on glass coverslips in 35 mm dishes, were transfected in Tris-buffered saline as described above, washed with chloroquine for 3 hrs. and incubated with DMEM containing serum. At 47 hrs. after removal of DNA/DEAE-dextran, cells were washed in PBS and fixed for 45 mins. at 22° C. in 2% formaldehyde, freshly prepared from paraformaldehyde, and then buffered in 0.05 M phosphate pH 7.5. The coverslips were rinsed in PBS for 20 mins. then soaked in 1% Triton X-100 in PBS for 20 mins. to permeablize the cells. Following two 10 minute rinses in PBS the coverslips were incubated for 1 hr. at 37° C. in a solution containing polyclonal rabbit anti-VP7 diluted 1:400 in PBS and rhodamine conjugated to wheat germ agglutinin (R-WGA) diluted 1:300 or 1:400. The cells were then rinsed exhaustively in PBS and incubated in a 1:300 dilution of secondary goat anti-rabbit IgG conjugated of fluorescein for 45 mins. at 37° C. Cells were photographed in the same plane of focus, with a Zeiss III RS photomicroscope, using appropriate filters for fluorescein or rhodamine.

In order to examine the ultrastructural morphology of untreated COS 7 and of SA11 infected MA104 cells (5.5 hrs post-infection, infected by known methods) coverslips were fixed in 2% glutaraldehyde in 0.1 M cacodylate buffer pH 7.4 for 45 mins. at 22° C. Cells were postfixed in 1% osmium tetroxide in cacodylate buffer, stained in 1% uranyl acetate, dehydrated in ethanol and embedded in resin prior to thin sectioning. Sections were stained with uranyl rinse and Reynolds lead satin for several minutes and then specimens were examined and photographed in a JEOL 100 CX electron microscope at 80 kv.

VII. Morphogenesis of Rotavirus Particles in SA11-infected MA104 Cells.

One novel feature of the rotavirus system is that the virus appears to be located primarily in elements of the ER. The distribution of virus particles in cells early in infection have been examined. At 5.5 hrs. post-infection, virus particles were found only in the ER; none were ever seen in the Golgi apparatus or in mitochondria. The viroplasm structures immediately adjacent to the RER were also evident and viral cores could be seen budding from the periphery of the viroplasm into the lumen of the RER. This envelope acquired from the RER membrane was subsequently lost and both enveloped and mature virions were visible in the lumenal space. VP7 has been located to the ER by immunoelectromicroscopy. In vitro translation studies have also shown it to be an integral membrane protein. Since the VP7 protein is found in mature virions and has only high-mannose oligosaccharides the prior art collectively shows that VP7 remains in the ER after translation. However, the mechanism by which VP7 is incorporated into the virus remains unknown. Thus, the rotavirus VP7 provides an opportunity to study the factors controlling the specific localization of proteins to the ER.

VIII. Ultrastructural Morphology of COS 7 Cells

In order to accurately interpret the localization of expressed VP7 protein products within COS 7 cells, it is necessary to examine the ultrastructual morphology and interrelationships of organelles in COS 7 cells, especially in the perinuclear region. These cells are characterized at their periphery by predominantly free polysomes crowding the cytoplasm and by numerous microvilli projecting from their cell surfaces. The cells are often multinucleate, have many lipid droplets, mitochondria, and a preponderance of organelles situated in close proximity to each other around the nucleus at the center of the cell. The perinuclear region is occupied by extensive branching endoplasmic reticulum, which contains numerous areas of transitional elements and smooth ER, that spatially intertwine with, but are distinct from, the extensive perinuclear Golgi apparatus. It is evident that portions of the Golgi apparatus can surround concentrated elements of the ER.

IX. Immunofluorescent Localization of VP7 Proteins in Transfected COS 7 Cells As described above, the gene encoding the VP7 protein was inserted into the vector pJC119 under the control of the SV40 late promoter to generate the plasmid pJC9. The expression of the VP7 protein from this gene was examined in transfected COS 7 cells to confirm the ER location of this protein. An indirect immunofluorescent procedure utilizing a secondary fluorescein-coupled goat anti-rabbit immunoglobulin and a primary monospecific polyclonal rabbit antiserum was used to localize VP7. A concomitant display of the lectin wheat germ agglutinin, conjugated to rhodamine (R-WGA), and known to specifically bind to sialic acid and terminal glucosamines in the Golgi appratus, permitted determination of whether VP7 was present in this organelle. The immunolocalization of VP7 expressed from pJC9 showed a distinct, arborizing, reticular pattern of fluorescein staining radiating from the nucleus, and a perinuclear concentration of stained, reticular material. This probably corresponds to the rough endoplasmic reticulum and to transitional elements of ER, spatially related to, but exlusive of, the Golgi apparatus. Nuclear staining is also evident. A staining pattern consisting of punctate material and a perinuclear localization, probably coincident with part of the Golgi apparatus and distinct from that of the VP7 localization, was seen. Thus, VP7 protein expressed from the wild type gene in pJC9 appears to localize to the ER and does not appear to reach the Golgi apparatus.

A series of plasmids containing mutations in the VP7 gene was also constructed (see FIG. 2). The deletions were constructed in order to study the role of the hydrophobic domains in VP7 synthesis. The location of VP7 expressed from these plasmids in COS 7 cells, was also examined by immunofluorescence. The deletion mutant 1-14 displayed extensive ER and perinuclear staining in regions distinct from that seen for R-WGA, similar to the wild type. In this mutant, the first ATG codon was deleted so that only the second initiation codon and the hydrophobic region following it could be utilized (FIG. 2). Another mutant studied, 2–8, in which the sequence following the first ATG codon was modified, showed results analogous to the wild type. In contrast, VP7 distribution in the mutants 42–61, 43–61 and 47–61, in which distal parts of the second hydrophobic domain were removed (FIG. 2), showed reticular staining and a distinct perinuclear distribution which coincide precisely with, or was a subset of, the R-WGA staining pattern. Thus it appeared that with these deletions, the mutant VP7 proteins reached the Golgi apparatus. Mutant 51–61, whose deletion removed a region distal to the hydrophobic domains, exhibited a staining pattern identical to the wild type, that of reticular staining and a perinuclear distribution distinct from that of the R-WGA staining pattern. It appears that the absence of the region coding for these amino acids was not sufficient to cause movement of VP7 out of the ER to the Golgi apparatus.

X. Intracellular Expression of VP7 Proteins

In order to confirm and extend the above results, VP7 expression from wild type and mutant genes was examined by immunoprecipitating radiolabeled proteins from cell lysates. Cells were transfected with plasmids containing the wild type gene (pJC9) or deletions 1–14, 2–8, 42–61, 43–61, 47–61 or 51–61 (FIG. 2). VP7 proteins were immunoprecipitated and displayed by gel electrophoresis before or after digestion with Endo-H and compared on the same gel alongside L-$^{35}$S-methionine labeled SAll infected MA104 cell lysate. No significant products were seen when either no DNA (FIG. 3) or the vector pJC119 was used as a control. However, the wild type and mutant genes all expressed a protein(s) precipitable with anti VP7 antiserum (FIG. 3 (−) tracks). In the case of the intact VP7 gene (pJC9) and the deletion 1–14, two products were seen in the absence of Endo-H, but the lower band was relatively minor and not always reproducible and its origin is uncertain. For mutants 42–61 and 51–61, two products were expressed and it is very likely that the lower molecular weight species was the non-glycosylated version of each protein. In the case of mutant 51–61 it is possible the lower molecular weight band arises from use of the third in-frame AUG as a start condon. This possibility is made less likely because for mutant 42–61 a similar unglycosylated band of the same size is secreted, implying the use of a functional signal which would not be translated if the third AUG was used as an initiation condon. The wild type' and mutant genes each expressed a product which was sensitive to Endo-H (FIG. 3 (+) tracks), indicating that they were glycosylated with N-linked, high mannose oligosaccharides. There was no significant intracellular pool of VP7 products that were resistant to Endo-H (FIG. 3). Cells were transfected and then incubated in the presence or absence of tunicamycin and the resulting unglycosylated products were slightly smaller in size than those treated with Endo-H (data not shown), again indicating the N-linked nature of the oligosaccharide. Taken together, these results imply that each mutant codes for proteins which retain a functional signal for translocation into the ER. For the 1–14 deletion, where only the second ATG and hydrophobic domain are retained, the latter probably constitutes the signal peptide. For the wild type and other mutants, the translocation signal domain cannot be specified since both ATG condons and hydrophobic regions are present. Transfected cells labeled for 2.5 hrs showed an overall similar pattern of expression of the intracellular VP7 products, and again there was little evidence of intracellular material resistant to Endo-H.

XI. Extracellular Products Expressed by VP7 Genes

Immunofluorescence studies indicated that for mutants 42–61, 43–61 and 47–61, VP7 staining co-localized with that of elements of the Golgi apparatus in COS 7 cells, indicating that these VP7 mutants were probably transported out of the ER. Therefore, the incubation media from all the transfected cell cultures described above were examined for secreted VP7 products. Three of the deletion mutants, 42–61, 43–61 and 47–61, affecting the distal region of the second hydrophobic domain produced VP7 molecules which were secreted (FIG. 4), in marked contrast to the behavior of the wild type VP7 gene (pJC9), and the other mutants, in particular 51–61 (FIG. 4). The latter differed by only four amino acids from the secreted mutant 47–61 (FIG. 2). In addition, the secreted VP7 products were Endo-H resistant (FIG. 4 (+) tracks), consistent with their passage through the Golgi apparatus and their modification to the complex type of carbohydrate. These results pertain to cells labeled for 4 hours. However, similar results were obtained in a 2.5 hour labeling period, indicating that secretion is an efficient process. The size of the VP7 which contained complex oligosaccharides was slightly larger than that of VP7 with the high mannose form of glycosylation (compare products in FIGS. 3 and 4 with markers). This was expected in view of the known higher molecular weight of complex N-linked oligosaccharides. Mutant 42–61 also secretes, based on its size, a non-glycosylated version of its mutant VP7 protein (FIG. 4). This was confirmed by another experiment where cultures transfected with mutants 42–61, 43–61 and 47–61 were subsequently treated with tunicamycin (FIG. 5). In control cells, those not treated with tunicamycin (FIG. 5, + and − tracks), the Endo-H resistant products were again secreted into the medium. However, in the presence of the drug, mutants 42–61, 43–61 and 47–61 secreted a lower molecular weight, unglycosylated (U) form of the protein (FIG. 5, (T) tracks). The product generated in the presence of tunicamycin (T) is identical in size to the unglycosylated product. No such bands were identified when vector without insert (pJC119) was used for transfection (FIG. 5, tracks 1–3). These results confirm that the Endo-H resistant products secreted into the medium by these mutants contain N-linked complex type of carbohydrate.

Analysis of the amino acid sequence of VP7 has shown the existence of two tandem amino terminal hydrophobic domains, within the first 50 amino acids. Each is preceded by an in-frame ATG condon. Since the first ATG is "weak" and the second one has the preferred consensus sequence for initiation, we cannot be sure which one is used for VP7 synthesis, and are unable to say where the reported signal peptide cleavage occurs. Since mutant 1-14, which deletes the first ATG condon, still produces a glycoprotein located in the ER, the second hydrophobic domain can provide signal peptide function. The N-terminal hydrophobic domains seem important in the maturation of rotaviruses since the hydrophobic nature is highly conserved in the VP7 glycoproteins of viruses infecting human, simian and bovine species, and therefore probably serve some role in anchoring this type of protein in the ER. There is no hydrophobic segment present at the carboxy terminus, a distinctive feature of the glycoproteins of plasma membrane maturing viruses. Our systematic generation of mutants affecting each or both of the hydrophobic regions was aimed at identifying the putative membrane anchor domain responsible for the ER location of the rotavirus VP7 glycoprotein.

The key observation is that in three of the deletion mutants extending into the second hydrophobic region, namely mutants 42-61, 43-61 and 47-61, the altered form of VP7 is secreted by transfected COS 7 cells and terminally glycosylated, a characteristic of a protein having traversed the normal secretory pathway. By contrast, neither the wild type gene product was secreted, nor were products from deletions which affected other parts of the molecule. The deletion 1-14, which completely removed the first hydrophobic domain and mutant 2-8, in which the eight amino terminal residues conserved in all four rotavirus VP7 serotypes were changed, efficiently expressed glycoprotein located to the ER. Similarly, removal of only 11 amino acids downstream of the hydrophobic domains in mutant 51-61, apparently was not sufficient to influence the movement of VP7 from the ER to the Golgi. The only effect was to perturb the efficiency of glycosylation, perhaps for steric reasons, since the glycosylation site in the altered products is brought closer to the hydrophobic domains.

The carbohydrate present on VP7 is of the high mannose type and is Endo-H sensitive, consistent with its ER location and the absence of terminal processing of the oligosaccharide. Analysis of VP7 glycoprotein processing shows that is does not reach the Golgi apparatus but rather accumulates in a subcompartment of the ER in a processing pathway quite different from VSV G-protein. It should be noted that there is a distinctly larger size of the secreted VP7s in mutants 47-61, 43-61 and 42-61, due to the terminal glycosyaation; they are also sensitive to tunicamycin and resistant to Endo-H. This observation underscores the ER location of wild type VP7 since it is apparent that its N-linked glycosylation can be modified and were the wild type molecule to have reached the Golgi apparatus, further processing and terminal glycosylation should have occurred. In the mutant VP7s, the efficiency of secretion appears to be high for two reasons. First, there is no Endo-H resistant material inside the cell after either 2.5 or 4 hrs of labeling. Second, the amount of material secreted is similar in amount to that seen intracellularly.

Other glycoproteins of the ER have been cloned and some sequenced. In the cases of HMG-CoA reductase and coronavirus El, there was no obvious homology between th N-terminal hydrophobic domains in these molecules and VP7, nor with the dual N-terminal hydrophobic domains in nonstructual rotavirus glycoprotein NCVP5. Cytochrome P-450, another ER protein, did not display any obvious homologies in its multiple hydrophobic domains. It should be noted, however, that HMG-CoA reductase, coronavirus El and cytochrome P-450 probably interact with the lipid bilayer much more extensively than does VP7, via multiple membrane spanning domains.

Since VP7 is not normally secreted, presumably there could be no specific ER receptor mediating its secretion, and therefore its movement along the secretory pathway in these cells is constitutive, rather than specific. This is the first demonstration of an alteration in the primary sequence which allows a naturally targeted ER molecule to be secreted, and shows unequivocally that glycoproteins can be secreted without the intervention of a specific receptor. Also of significance is that an unglycosylated, mutant VP7 is efficiently secreted. The precise reason(s) for the secretion of VP7 in the mutants 42-61, 43-61 and 47-61 is not yet clear. It could be that an anchor region has been shortened so that it no longer functions, that a positive signal for ER location has been disrupted, or that a peptidase cleavage site, e.g., the Ala-Tyr-Ala sequence at residues 66-68, has been brought into proximity of the aminopeptidase used for signal peptide cleavage. These results become particularly interesting when juxtaposed with several other observations. Firstly, some normally soluble molecules of the ER remain in the ER, whereas soluble VP7 is secreted. Secondly, influenza neuraminidase is anchored in the membrane by an $NH_2$-terminal hydrophobic domain, but this molecule, unlike VP7, is exported to the plasma membrane. From the above, it is concluded that the region of the second hydrophobic domain of VP7 not only serves to anchor the protein in the membrane but may also contain the positive and specific signal for maintaining the protein in the ER.

XII. Stably Transformed Secreting Cells

A cloned cell line which is stably transformed with mutant 47-61, for example, is desirable in order to obtain a continuous secretor of the mutant VP7 neutralizing antigen as a source for purifying the molecule in larger quantity. To this end, COS-7 cells are co-transfected with pJC9 carrying mutant 47-61 and pSV2-neo, a eukaryotic expression vector containing the neomycin resistance gene. Clones isolated and grown in the presence of the antibiotic G418 are screened with anti VP7 antiserum by known filter immuno blotting techniques allowing large scale screening. In the event that the high mannose form of glycosylation, as distinct from the complex form shown to be present on the secreted product of mutants 43-61 and 47-61, is important in the neutralizing antigenicity, a cloned stably transformed cell line of the transfected somatic cell mutant of chinese hamster ovary cells (CHO) called Lec 1, which is incapable of synthesizing the complex form of glycosylation, may be used.

An alternative approach to obtain the high mannose form of glycosylation on the secreted mutant VP7 proteins, is to transform yeast cells processing a Sec 18-1 genetic background with a high copy number expression plasmid containing the gene for rotavirus VP7 mutants 43-61 or 47-61. This temperature sensitive yeast mutant blocks glycosylation in a form called "mannose$_8$" and should produce a soluble mutant 47-61 VP7 with glycosylation similar to that found in wild type VP7 virus.

XIII. Nature of the Membrane Anchoring Region

In establishing that the region downstream of the hydrophobic domains of VP7 has no endoplasmic reticulum anchoring ER function; the entire coding sequence of VP7, 5' to the Ncol restriction site was removed, which deletes both hydrophobic domains into to leaving only the sequence coding for the body of VP7, and its glycosylation site. When a rough endoplasmic reticulum translocation signal that is known to be cleaved, e.g. the coding region of the amino terminally located hydrophobic domain from influenza hemagglutinin, is joined to sequence coding for the body of V7 (pHA-VP7) transfection and expression of this construct allows analysis of VP7 behavior in the absence of any retained amino terminal hydrophobic domain. Mutants 43-61, 47-61 and the construct pHA-VP7 show identical behavior. Following a 4 hour labeling period, 46-50 hours after transfection, all intra-cellular precipitable VP7 was Endo H sensitive. Efficient secretion occurred as well and all secreted VP7 was Endo H resistant. As such, a soluble, cell secreted neutralizing VP7 antigen of rotavirus can be formed by the substitution of gene sequence coding for the two hydrophobic domains of the VP7 protein, with a translocation signal that is known to be cleaved. These results again illustrate the constitutive nature of the secretion of VP7 in the absence of any RER anchoring sequence and underscores the lack of targetting information in the more distal portions of VP7.

As will be readily apparent to those skilled in the art, the invention may be used in other specific forms or for other purposes without departing from its spirit or central characteristics. The present embodiments are therefore to be considered as illustrative and not restrictive, the scope of the invention being indicated by the claims rather than by the foregoing description, and all embodiments which come within the range of equivalence of the claims are intended to be embraced.

What is claimed is:

1. A neutralizing antigen of rotavirus comprising a VP7 protein modified to be cell secreted by the removal of coding sequences from the codon for the mature N-terminus to the codom for amino acid number 6I in the open reading frame and the addition of a cleavable translocation signal allowing transport into the secretory compartment of the cell and subsequent secretion of the antigen.

2. The antigen of claim 1 which reacts with antibodies to VP7.

3. A neutrallizing antigen of rotavirus comprising a VP7 protein modified to be cell secreted and soluble in an aqueous medium by the removal of coding sequences from the codon for the mature N-terminus to the codon for amino acid number 61 in the open reading frame and the addition of a cleavable translocation signal allowing transport into the secretory compartment of the cell and subsequent secretion of the antigen.

4. The antigen of claim 3 which reacts with antibodies to VP7.

5. A neutrallizing antigen of rotavirus comprising a VP7 protein modified to be cell secreted by the removal of coding sequences for amino acid sequences selected from the group consisting of 42-61, 43-61 and 47-61 in the open reading frame and the addition of a cleavable translocation signal allowing transport into the secretory compartment of the cell and subsequent secretion of the antigen.

6. The antigen of claim 5 which reacts with antibodies to VP7.

7. The antigen of claim 5 consisting essentially of said modified VP7 protein.

8. A neutralizing antigen of rotavirus comprising a VP7 protein modified to be cell secreted and soluble in an aqueous medium by the removal of coding sequences for the amino acid sequences selected from the group consisting of 42-61, 43-61 and 47-61 in the open reading frame and the addition of a cleavable translocation signal allowing transport into the secretory compartment of the cell and subsequent secretion of the antigen.

9. The antigen of claim 8 which reacts with antibodies to VP7.

10. The antigen of claim 8 consisting essentially of said modified VP7 protein.

11. The antigen of claim 1 consisting essentially of said modified VP7 protein.

12. The antigen of claim 3 consisting essentially of said modified VP7 protein.

* * * * *